(12) United States Patent
Chambers et al.

(10) Patent No.: US 6,477,907 B1
(45) Date of Patent: Nov. 12, 2002

(54) DETECTION OF EXPLOSIVES IN SOILS

(75) Inventors: William B. Chambers, Edgewood, NM (US); Philip J. Rodacy, Albuquerque, NM (US); James M. Phelan, Bosque Farms, NM (US); Ronald L. Woodfin, Sandia Park, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/603,729

(22) Filed: Jun. 23, 2000

Related U.S. Application Data

(63) Continuation-in-part of application No. 09/205,158, filed on Dec. 3, 1998, now abandoned.

(51) Int. Cl.[7] ............................................... G01N 33/00
(52) U.S. Cl. ................... 73/866; 73/863.21; 73/863.23; 73/864.81; 436/28
(58) Field of Search ............................ 73/866, 863.11, 73/863.12, 863.21, 863.23, 864.81, 31.02, 23.41; 436/28

(56) References Cited

U.S. PATENT DOCUMENTS

| | | | |
|---|---|---|---|
| 4,573,354 A | * | 3/1986 | Voorhees et al. ......... 73/863.21 |
| 4,709,577 A | * | 12/1987 | Thompson ................. 73/40.7 |
| 5,411,087 A | * | 5/1995 | Taylor ...................... 73/863.11 |

FOREIGN PATENT DOCUMENTS

| | | | |
|---|---|---|---|
| JP | | 325832 | * 12/1998 |

\* cited by examiner

Primary Examiner—Hezron Williams
Assistant Examiner—Nashmiya Fayyaz
(74) Attorney, Agent, or Firm—Elmer A. Klavetter

(57) ABSTRACT

An apparatus and method for detecting explosive-indicating compounds in subsurface soil. The apparatus has a probe with an adsorbent material on some portion of its surface that can be placed into soil beneath the ground surface, where the adsorbent material can adsorb at least one explosive-indicating compound. The apparatus additional has the capability to desorb the explosive-indicating compound through heating or solvent extraction. A diagnostic instrument attached to the probe detects the desorbed explosive-indicating compound. In the method for detecting explosive-indicating compounds in soil, the sampling probe with an adsorbent material on at least some portion of a surface of the sampling probe is inserted into the soil to contact the adsorbent material with the soil. The explosive-indicating compounds are then desorbed and transferred as either a liquid or gas sample to a diagnostic tool for analysis. The resulting gas or liquid sample is analyzed using at least one diagnostic tool selected from the group consisting of an ion-mobility spectrometer, a gas chromatograph, a high performance liquid chromatograph, a capillary electrophoresis chromatograph, a mass spectrometer, a Fourier-transform infrared spectrometer and a Raman spectrometer to detect the presence of explosive-indicating compounds.

13 Claims, 2 Drawing Sheets

DETECTION OF EXPLOSIVES IN SOILS

This application is a continuation-in-part of U.S. patent application Ser. No. 09/205,158, filed on Dec. 3, 1998 now abandoned.

This invention was made with Government support under Contract No. DE-AC04-94AL85000 awarded by the Department of Energy. The Government has certain rights in the invention.

BACKGROUND OF THE INVENTION

The invention relates to a method and apparatus for detecting trace amounts of explosives in soils and, more particularly, for detecting explosive-indicating compounds and munitions in near-surface soils.

Most methods for analyzing and detecting explosives or organic compounds that are indicative of the presence of explosives in subsurface soil require obtaining a soil sample, removing the soil sample to another location, extracting the organic compounds and analyzing the extracted supernatant with a standard chemical diagnostic technique to determine if explosive compounds are present. These methods have been generally designed to detect the presence of explosives for environmental remediation with sensitivities generally greater than approximately one part per million. Problems in reliable detection can occur when a soil sample is removed from its subsurface, in situ environment and transported to another location for subsequent processing steps wherein the explosive compounds are separated from the soil and then analyzed. Although steps can be taken to address these problems, the. compounds to be detected in the soil are subject to degradation, volatilization and contamination between the step of sampling and subsequent analysis at a separate location. Additionally, concentrations of the explosive compounds can be diluted below the sensitivity of the detection analysis equipment.

In order to detect buried landmines and unexploded ordnance (UXO), the detection apparatus must have a sensitivity significantly less than one part per million (Phelan, J. and Webb, S., Sandia National Laboratories report no., SAND97-1426, Sandia National Laboratories, Albuquerque, N.Mex., 1997). This is because the explosive compounds are generally not directly exposed to the soil but are contained within the landmine or UXO and diffuse out slowly. Additionally, it is useful to have a field portable apparatus and method that is mobile and functional in situ (below the soil surface) to provide rapid classification of explosive compounds, landmines, and UXO.

The U.S. Environmental Protection Agency (EPA) has developed a method for analyzing soils for explosive compounds. EPA Method 8330 describes a method for analysis of concentration of explosive residues in a water, soil or sediment matrix using high performance liquid chromatography. Soil samples are removed from their environment and generally transported to another location for analysis. Aqueous samples are diluted with methanol, filtered, and separated on a standard column. Soil and sediment samples are first extracted using acetonitrile in an ultrasonic bath and then analyzed similarly to the aqueous samples. The separation of the explosive compounds from the soil sample therefore occurs after the soil sample has been removed from its environment, thereby providing the opportunity for contamination, degradation and volatilization and thereby false readings. For the explosive residue chemical compounds of interest, such as trinitrotoluene (TNT), dinitrotoluene (DNT), octahydro-1,3,5,7-tetranitro-1,3,5,7-tetrazocine (HMX), and hexahydro-1,3,5-trinitro-1,3,5-triazine (RDX), the sensitivity in field contaminated soils is only approximately 1 to approximately 900 parts per million by weight.

Walsh and Jenkins (Marianne Walsh and Thomas Jenkins, U.S. Army Corp of Engineers, Special Report 91-7, June 1991) describe a method for field screening of one common explosive compound, referred to as hexhydro-1,3,5-trinitro-1,3,5-triazine (RDX), found in soils. In this method, similar to one developed for trinitrotoluene (TNT), a mild solvent and Greiss color reagent is added to a soil sample to produce a color change and specific absorbance when the explosive compound of interest is present. The method is utilized for RDX concentrations of approximately 1 part per million or higher.

Sausa (U.S. Pat. No. 5,759,859, issued on Jun. 2, 1998) describes a cone penetrometer apparatus for continuously measuring the concentration of energetic materials, such as explosive compounds, in potentially-contaminated soils using two lasers, one for decomposing an energetic material into NO (nitrogen oxide) fragments and the other to detect the NO. Although this is an in situ method for detecting NO, the sensitivity of the method is not provided. The method does not directly detect explosive compounds such as TNT, DNT, RDX, and HMX but merely the NO compound from the thermal fragmentation process, which could also be a thermal fragmentation by-product from other chemicals, such as fertilizers. The apparatus utilizes a truck to house the sensor components as well as a hydraulic press that is used to pull and push the penetrometer in or out of the ground.

Pomeroy (U.S. Pat. No. 4,641,566, issued on Feb. 10, 1987) describes an indirect method for detecting buried landmines where an area of interest is sprayed with a leach of ionized metal that is assumed to concentrate on an impervious object such as rocks or an impervious landmine. An array of detectors is then used to detect the enhanced concentration of ionized metal. Difficulties may arise in determining whether landmines are present when impervious objects such as rocks or man-made objects other than landmines are present in the subsurface or when the hydrological characteristics of the soil prevent uniform transport of the leach.

Useful for the detection of explosive compounds, landmines and UXO would be a method and apparatus for rapid analysis of soil in the subsurface soil and to detect explosive compounds originally contained in landmines or UXO or explosive chemical compounds indicative of the presence of explosives, landmines or UXO.

SUMMARY OF THE INVENTION

According to the present invention, an apparatus for detecting explosive-indicating compounds in soil is provided, comprising a sampling means for exposing an adsorbent material to soil, said adsorbent material capable of adsorbing at least one explosive-indicating compound, a means for desorbing said explosive-indicating compounds, and a diagnostic means for detecting said explosive-indicating compounds. The sampling means comprises an outer sheath and an inner probe, wherein the inner probe can be exposed to soil and wherein at least some portion of the surface of the inner probe is covered with the adsorbent material.

The desorbing means can be a solvent or a heating means, such as radiative heating, an inductive electrical circuit, a resistive electrical circuit, or a hot gas. The diagnostic means comprises at least one chemical detector. The chemical detector can be a mass detector, such as a mass spectrometer, acoustic wave device or quartz crystal microbalance; an optical-based detector, such as an infrared detector, an ultraviolet-visible detector, a refractive index detector, a fluorescence detector, a chemiluminescence detector or a Raman detector; a charged-mass detector, such as a magnetic sector analyzer, a time of flight analyzer, a quadrupole mass filter or an ion trap/ion resonance mass filter; a thermal conductivity detector, an electron capture detector, an immunoassay detector; or any chemical detector common to those skilled in the art in detecting organic chemicals. The diagnostic means can include both a chemical detector as well as a separations means, such as commonly present in chromatographic diagnostic instruments. The diagnostic means can be at least one diagnostic tool selected from a group consisting of an ion-mobility spectrometer, a gas chromatograph, a high performance liquid chromatograph, a capillary electrophoresis chromatograph, a mass spectrometer, a Fourier-transform infrared spectrometer, a Raman spectrometer or combination thereof.

The apparatus can be a field-portable instrument wherein the sampling means is connected to the diagnostic means or the sampling means can be unconnected from the diagnostic means and the sampling means transported to the location of the diagnostic means for analysis.

A method for detecting explosive-indicating compounds in soil is also part of the present invention, wherein a sampling means with an adsorbent material on at least some portion of a surface of the sampling means is inserted into the soil to contact the adsorbent material with the soil. The explosive-indicating compounds are then desorbed and transferred as either a liquid or gas sample to a diagnostic tool for analysis. An aqueous solvent can be added to the volume around the adsorbent material to enhance transfer of the explosive-indicating compounds in the soil to the adsorbent material. The explosive-indicating compounds are desorbed from the adsorbent material by a solvent or by heating. The resulting gas or liquid sample is analyzed by a diagnostic means. The diagnostic means comprises at least one chemical detector. The chemical detector can be a mass detector, such as a mass spectrometer, acoustic wave device or quartz crystal microbalance; an optical-based detector, such as a infrared detector, an ultraviolet-visible detector, a refractive index detector, a fluorescence detector, a chemiluminescence detector or a Raman detector; a charged-mass detector, such as a magnetic sector analyzer, a time of flight analyzer, a quadrupole mass filter or an ion trap/ion resonance mass filter; a thermal conductivity detector, an electron capture detector, an immunoassay detector; or any chemical detector common to those skilled in the art in detecting organic chemicals. The diagnostic means can include both a chemical detector as well as a separations means, such as commonly present in chromatographic diagnostic instruments. The diagnostic means can be selected from the group consisting of an ion-mobility spectrometer, a gas chromatograph, a high performance liquid chromatograph, a capillary electrophoresis chromatograph, a mass spectrometer, a Fourier-transform infrared spectrometer, and a Raman spectrometer to detect the presence of explosive-indicating compounds.

DESCRIPTION OF SPECIFIC EMBODIMENTS

Figure 1:
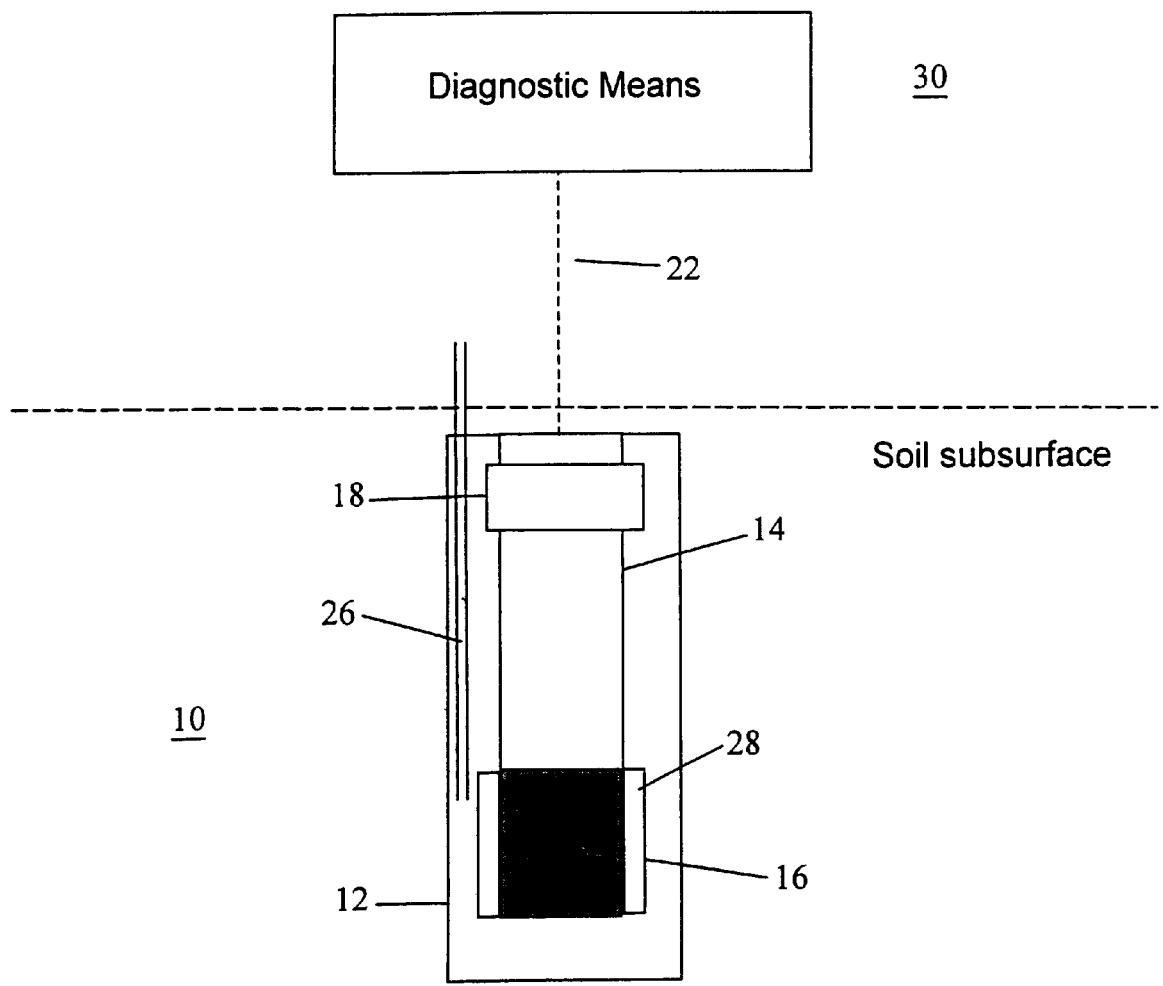
FIG. 1 shows one embodiment of an apparatus of the present invention.

The apparatus and method of the present invention are used to detect explosive-indicating chemicals or compounds, in subsurface soil containing those compounds, either from the vapor or aqueous phase of the soil or extractable from the solid phase of the soil matrix. The explosive-indicating compounds can originate from direct contamination of the soil by these compounds or originate from explosives, landmines or any UXO.

Explosive molecules are semi-volatile organic compounds. The explosive compounds, or their degradation products, used in military and industrial applications, and therefore present in soil where explosives, landmines and UXO are present or where explosion events have occurred to directly contaminate the soil with explosive compounds, include, but are not limited to, octahydro-1,3,5,7-tetranitro-1,3,5,7-tetrazocine ($C_4H_8N_8O_8$ or HMX), hexahydro-1,3,5-trinitro-1,3,5-triazine ($C_3H_6N_6O_6$ or RDX), 1,3,5-trinitrobenzene ($C_6H_3N_3O_6$ or TNB), 1,3-dinitrobenzene ($C_6H_4N_2O_4$ or DNB), methyl-2,4,6-trinitrophenylnitramine ($C_7H_5N_5O_8$ or Tetryl), nitrobenzene ($C_6H_5NO_2$ or NB), 2,4,6-trinitrotoluene ($C_7H_5N_3O_6$ or TNT), 2,4-dinitrotoluene ($C_7H_6N_2O_4$ or 24DNT), 2,6-dinitrotoluene ($C_7H_6N_2O_4$ or 26DNT), o-nitrotoluene ($C_7H_7NO_2$ or 2NT), m-nitrotoluene ($C_7H_7NO_2$ or 3NT), p-nitrotoluene ($C_7H_7NO_2$ or 4NT), nitroglycerin ($C_3H_5N_3O_9$ or NG), 4-amino-2,6-dinitrotoluene ($C_7H_7N_3O_4$ or 4-Am-DNT), 2-amino-4,6-dinitrotoluene ($C_7H_7N_3O_4$ or 2-Am-DNT), and pentaerythritol tetranitrate ($C_5H_8N_4O_{12}$ or PETN). The presence of these compounds can indicate the presence of explosives or munitions, such as landmines or UXO, which are present in the soil subsurface.

According to the present invention, a sampling means is exposed directly to the soil and explosive-indicating compounds in the soil below the ground surface, that is the subsurface soil. The compounds are adsorbed onto an adsorbent material that is part of the sampling means and later desorbed and transferred to a diagnostic means for analysis. In the apparatus and method of the present invention, the explosive-indicating compounds in the soil are sampled directly beneath the ground surface (i.e., the subsurface), eliminating the potential for sample contamination or loss from volatilization or degradation. Problems in reliable detection can occur when a soil sample is removed from its subsurface, in situ environment and transported to another location for subsequent processing steps wherein the explosive compounds are separated from the soil and then analyzed. The soil sample can be contaminated, degraded or volatilized between sampling and analysis. Additionally, concentrations of the explosive compounds can be diluted below the sensitivity of the detection analysis equipment. These potential problems are mitigated in the present invention because the explosive compounds in the soil are collected directly by the sampling means and transferred to a diagnostic means.

According to the present invention, the apparatus and method that can be used to detect explosive materials in a soil or other granular or particulate medium comprises a sampling means and a diagnostic means. The sampling means is a probe that can be inserted into the soil in an area where explosive materials are suspected. This can be an area where landmines or unexploded ordnance (UXO) are expected to be present or an area where the presence of explosive material residue is suspected. The sampling means collects a sample of the explosive-indicating compounds present in the sampling location and then transfers this concentrated sample of explosive-indicating compounds to a diagnostic means for rapidly analyzing said sample. The sampling means can be operated independently to collect the compounds in the soil subsurface, wherein the sampling means is then removed from the soil location and then transported to another location where the compounds can be transferred to the diagnostic means for analysis and detection. Alternatively, the sampling means can be operated in conjunction with the diagnostic means wherein the explosive-indicating compounds are collected in the soil subsurface and then transferred directly to the diagnostic means at or near the site where the sampling means was inserted into the soil. The diagnostic means analyzes the sample provided by the sampling means to detect these explosive-indicating organic compounds collected by the sampling means and provides an output signal, either electronic, audio, visual or a combination thereof, that indicates that an explosive compound is detected in the area in Which the sampling means was placed.

Sampling means 10 (illustrated in FIG. 1) comprises an outer sheath 12 and an inner probe 14, wherein the inner probe 14 can be exposed to soil either by, in one embodiment, retracting the outer sheath 12 or, in another embodiment, by inserting the inner probe 14 through the outer sheath 12 into the soil. An important function of the outer sheath 12 is to protect the inner probe 14, for example, when the inner probe 14 is inserted into the soil. On some portion of the surface of the inner probe 14 is a solid-phase adsorbent material 16 which, when placed in contact or near the soil, functions to adsorb and concentrate explosive-indicating molecules from the soil onto the adsorbent material 16. Adsorbent materials for the analysis and detection of explosive-indicating compounds include organic polymeric films such as polyethylene, polystyrene and polystyrene-divinylbenzene (PS-DVB). The inner probe 14 is retracted within the outer sheath 12 to a desorption zone within the sampling means 10 wherein the adsorbed molecules are desorbed by a desorbing means 18. The desorbing means 18 can be a heating means to thermally desorb the adsorbed explosive-indicating molecules, producing a vapor sample potentially containing the explosive-indicating molecules. The desorbing means 18 can alternatively be a solvent to extract the adsorbed molecules, producing a liquid sample potentially containing the explosive-indicating molecules.

The sample produced by the desorbing means 18 is transferred to the diagnostic means 30 that analyzes the sample for at least one explosive-indicating chemical compound. The diagnostic means 30 comprises at least one chemical detector. The chemical detector can be a mass detector, such as a mass spectrometer, acoustic wave device or quartz crystal microbalance; an optical-based detector, such as a infrared detector, an ultraviolet-visible detector, a refractive index detector, a fluorescence detector, a chemiluminescence detector or a Raman detector; a charged-mass detector, such as a magnetic sector analyzer, a time of flight analyzer, a quadrupole mass filter or an ion trap/ion resonance mass filter; a thermal conductivity detector, an electron capture detector, an immunoassay detector; or any chemical detector common to those skilled in the art in detecting organic chemicals. The diagnostic means 30 can include both a chemical detector as well as a separations means, such as commonly present in chromatographic diagnostic instruments. Specific diagnostic means 30 include an ion-mobility spectrometer, a gas chromatograph, a high performance liquid chromatograph, a capillary electrophoresis chromatograph, a mass spectrometer, a Fourier-transform infrared spectrometer, a Raman spectrometer or other means that can separate and detect explosive-indicating compounds. Preferred is a detector that can detect the explosive-indicating compounds at part-per-billion concentrations or less and that produces an electronic, visual, or audio output signal when an explosive compound is detected.

In one embodiment, illustrated in FIG. 1, a permeable screen or perforated sleeve 28 can be placed over the adsorbent material 16; the permeable screen 28 must be permeable to water and vapor and be made of stainless steel or another chemically inert material. The permeable screen 28 prevents abrasion to the adsorbent material 16 by direct contact of the soil with the adsorbent material 16 as well as preventing cross contamination between successive samples.

In another embodiment, the sampling means 10 contains a means 26, such as a liquid reservoir and pump attached to hollow tubing, for introducing a solvent to the volume around the solid-phase adsorbent material 16 or permeable screen 28 to provide a liquid medium for extraction and transfer of the explosive-indicating compounds from the surrounding soil to the adsorbent material. For detection and analysis of explosive-indicating compounds, the solvent can be hot water or steam, or a water-based solution containing a miscible organic solvent such as methanol, ethanol, acetone, or acetonitrile. The solvent can also contain water-soluble salts to aid in the extraction and transfer of explosive-indicating compounds from the soil to the solid-phase adsorbent. The sample means 10 can also contain a means for pumping air, such as a standard pump with hollow tubing allowing air contact with the outside environment, from a region between the screen/sleeve 28 and the adsorbent material 16 to provide a negative pressure (air pressure less than atmospheric) such that the vapor phase explosive compounds or molecules flow from the volume outside the permeable screen 28, through the screen and into contact with the adsorbent material 16.

In one aspect of the apparatus of the present invention, the sampling means is connected directly to the diagnostic means by a connecting means, providing a field portable apparatus for rapid detection of subsurface explosives, particularly detection of buried landmines and unexploded ordnance. The connecting means, such as hollow tubing, functions to allow the liquid or gaseous sample from the desorbing means to be transported to the diagnostic means. Alternatively, the sampling means is not directly connected to the diagnostic means but is transported to the diagnostic means wherein the sample of explosive-indicating compounds is analyzed by the diagnostic means.

In another embodiment of the invention, the method of the present invention relies on contact of a sampling means 10 with soil suspected of containing one or more explosive-indicating compounds and in contact with the subsurface soil. Subsurface, in situ contact is generally accomplished by inserting the sampling means 10 in the subsurface soil, wherein said insertion can be just below the top of the soil surface (for example, one or more inches) to several feet or more in the subsurface. An adsorbent material 16 contained in the sampling means is exposed to the subsurface soil, either by retracting the outer sheath 12 or by moving the inner probe 14 through the outer sheath 12. The adsorbent material 16, when contacted with the soil, that is the soil vapor, the soil moisture, or the solid soil matrix, adsorbs some quantity of explosive-indicating molecules contained in the soil. An important part of the method of the present invention is to have subsurface, in situ contact between the adsorbent material and the soil potentially containing the explosive-indicating compounds.

In one embodiment, an aqueous solvent is added by means 26 to the soil in the area of contact between the soil and sampling means 10 to enhance transfer of the explosive-indicating compounds potentially present in the soil to the adsorbent material 16, solubilizing the explosive-indicating molecules adsorbed on the soil. More preferred is to add an aqueous solvent at an elevated temperature to aid in solubilizing the explosive-indicating molecules in the soil.

The adsorbent material 16 is chosen to have properties that enhance selectivity of the explosive-indicating molecules to be detected. Adsorbent materials for the analysis and detection of explosive-indicating compounds include organic polymeric films such as polyethylene, polystyrene and polystyrene-divinylbenzene. The explosive-indicating molecules, if any, on the adsorbent material 16 are desorbed to produce either a liquid or vapor sample containing any explosive molecules present. A liquid sample is produced if the desorbing means 18 is a solvent, such as methanol, ethanol, acetone, or acetonitrile. A vapor sample is produced if the desorbing means 18 is a heating means to thermally desorb the explosive molecules. Heating can be achieved through the application of resistive or. inductive electrical circuits, radiative energy, hot gasses generated by combustion reactions, or by exothermic reaction of chemical mixtures. The sample potentially containing explosive-indicating molecules is transferred to diagnostic means 30 for analyzing the sample to determine if explosive-indicating molecules are present. The diagnostic means 30 comprises at least one chemical detector. The chemical detector can be a mass detector, such as a mass spectrometer, acoustic wave device or quartz crystal microbalance; an optical-based detector, such as a infrared detector, an ultraviolet-visible detector, a refractive index detector, a fluorescence detector, a chemiluminescence detector or a Raman detector; a charged-mass detector, such as a magnetic sector analyzer, a time of flight analyzer, a quadrupole mass filter or an ion trap/ion resonance mass filter; a thermal conductivity detector, an electron capture detector, an immunoassay detector; or any chemical detector common to those skilled in the art in detecting organic chemicals. The diagnostic means 30 can include both a chemical detector as well as a separations means, such as commonly present in chromatographic diagnostic instruments. Specific diagnostic means 30 include an ion-mobility spectrometer, a gas chromatograph, a high performance liquid chromatograph, a capillary electrophoresis chromatograph, a mass spectrometer, a Fourier-transform infrared spectrometer, a Raman spectrometer or other means that can separate and detect explosive-indicating compounds. The transfer of the sample can occur directly from the sampling means to the diagnostic means where the diagnostic means is a field portable diagnostic system. Alternatively, the sampling means with the adsorbed explosive compounds can be transferred to another location where the explosive-indicating compounds are desorbed and transferred to the diagnostic means.

An important advantage of the apparatus and method of the present invention is that at least one phase of the soil is contacted in situ in the soil subsurface with the adsorbent means, preventing contamination, volatilization, or degradation of the sample that can occur if a soil is first removed from the environment and taken to another location to obtain a sample for analysis.

Subsurface, in situ contact, adsorption, and desorption also facilitates rapid analysis. Explosive detectors in current use generally are vapor-phase detectors that have no means of sampling buried sources. Data by Phelan and Webb (Phelan, J. and Webb, S., Sandia National Laboratories report No., SAND97-1426, Sandia National Laboratories, Albuquerque, N.Mex., 1997) demonstrate that approximately 99.99999% of the explosive released from a buried source is adsorbed by the soil or dissolved in the soil pore water, requiring detection limits of these materials in the vapor phase to generally be significantly lower than those currently available.

Although the concentration of the explosive compounds can be estimated, accurate determination of the concentration is not necessary for the invention. An important function of the apparatus and method of the present invention is to rapidly determine if explosive compounds are present. The apparatus and method of the present invention can work in conjunction with other detectors such as magnetometers and ground penetrating radar that can locate subsurface objects but cannot distinguish explosive munitions such as landmines or UXO from other objects.

For example, in order to detect landmines, the probe is inserted in the subsurface around the location in which the landmine presence is suspected. The adsorbent material on the inner probe is contacted with the soil. After adsorption onto the adsorbent material, the explosive-indicating molecules are subsequently desorbed and the sample analyzed by a suitable diagnostic means. The method of the present invention indicates whether any explosive material is present, thus indicating the presence of explosive material residue, a landmine, or other UXO. Additionally, other chemicals can also be detected by the apparatus and method of the present invention; to detect other chemicals, an adsorbent material which can adsorb the specific chemicals to be detects must by utilized by the sampling means.

This method increases the sensitivity of detection significantly over existing sensors, such as cone penetrometer sensor probes which have a sensitivity of approximately 500–1000 parts per billion of TNT. In the method of the present invention, the sensitivity is less than approximately ten part-perbillion of TNT. Additionally, in the present invention, the explosive molecules are captured intact, rather than as thermal breakdown products, yielding a more accurate identification. In methods where the explosive molecules are fragmented, such as by a laser, the resulting molecule to be detected, such as NO, could also be a product from another, non-explosive material such as fertilizer.

EXAMPLES

Example 1

Soil samples were taken in the vicinity (1–12" distant) of buried landmines and were independently determined to have explosive concentrations of 4 and 40 parts-per-billion of 2,4-DNT and TNT, respectively, by standard analytical laboratory techniques. Portions of the soil samples were subsequently placed in glass vials and sealed with a septum lined cap. Some of the vials had water added prior to sealing. The vials were heated and a commercial (SUPELCO, Inc.) solid-phase microextraction (SPME) "fiber", bearing a thin-film solid phase adsorbent coating of polystyrene-divinylbenzene, was inserted into the vial "headspace" (in the vapor above the soil level). The fiber was withdrawn from the vial after 30 minutes and inserted into the heated inlet of a gas chromatograph equipped with electron-capture detector. The heated inlet served as a thermal desorption means. No detector response was observed for the dry soil samples. For the vials which had water added, a significant signal was detected at the chromatographic retention time for both 2,4-DNT and TNT. An even greater signal was detected when the SPME fiber was inserted directly into the soil/water mixture for adsorption and analysis.

Example 2

Figure 2:
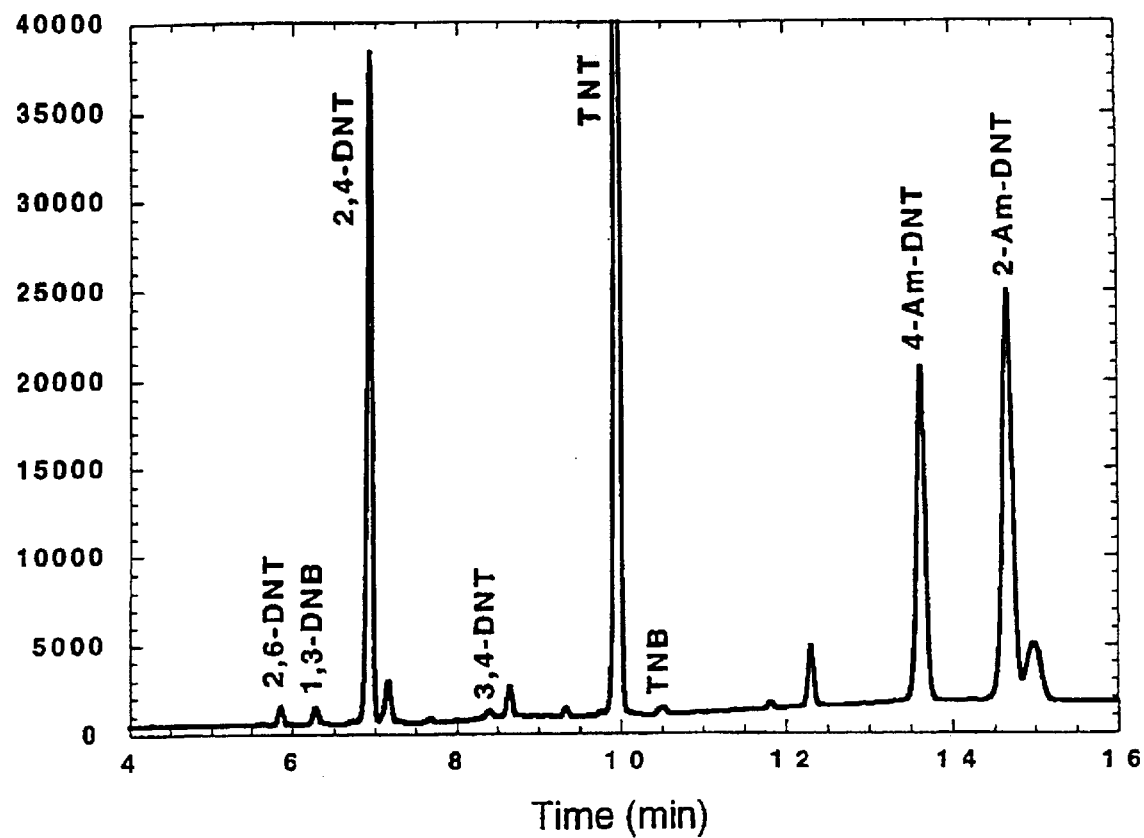
FIG. 2 shows a chromatograph indicating the detection of explosive-indicating compounds.

An inner sampling probe according to the present invention, with the adsorbent polystyrene-divinylbenzene coated onto the outer surface of one end of the probe, was housed in an outer, enclosed, pointed, perforated metal tube. Approximately 12 of these devices were inserted into the ground in the vicinity of buried landmines at depths of approximately 2–6 inches. Soil gas was drawn through the perforated tubes across the solid phase adsorbent coating on the sampling probe using a small air pump for periods of hours to days. The devices were subsequently disassembled and the organic compounds on the adsorbent coating were thermally desorbed and analyzed for adsorbed explosives by gas chromatography. Explosive molecules, including 2,4-DNT, TNT, 4-amino-2,6-dinitrotoluene (4-Am-DNT), 2-amino-4,6-dinitrotoluene (2-Am-DNT), DNB, and TNB, were detected in the soil gases by gas chromatography; a typical chromatograph showing the detection of these explosive-indicating compounds is shown in FIG. 2.

The invention has been described in detail above and in the specific examples. Further variations will be apparent to those skilled in the art. The true scope of the invention is to be found in the appended claims.

We claim:

1. A field-portable apparatus for detecting at least one semi-volatile explosive-indicating compound in subsurface soil, comprising, an inner probe having an adsorbent material contacting at least a portion of the surface of said inner probe, said adsorbent material selected from the group consisting of polyethylene, polystyrene and polystyrene-divinylbenzene, said adsorbent material capable of adsorbing at least one semi-volatile, explosive-indicating compound, said at least one explosive-indicating compound selected from the group consisting of octahydro-1,3,5,7-tetranitro-1,3,5,7-tetrazocine, hexahydro-1,3,5-trinitro-1,3,5-triazine, 1,3,5-trinitrobenzene, 1,3-dinitrobenzene, methyl-2,4,6-trinitrophenylnitramine, nitrobenzene, 2,4,6-trinitrotoluene, 2,4-dinitrotoluene, 2,6-dinitrotoluene, o-nitrotoluene, m-nitrotoluene, p-nitrotoluene, nitroglycerin, 4-amino-2,6-dinitrotoluene, 2-amino-4,6-dintrotoluene, and pentaerythritol tetranitrate;

an outer sheath enclosing said inner probe, said outer sheath capable of being retracted to expose said inner probe and adsorbent material to subsurface soil when inserted under ground surface;

means for desorbing in situ said at least one semi-volatile, explosive-indicating compound, said desorbing means, said means for desorbing in situ said at least one semi-volatile, explosive-indicating compound selected from a solvent, an inductive electrical circuit, a resistive electrical circuit, radiative energy, and a hot gas; and diagnostic means for detecting said at least one semi-volatile, explosive-indicating compound.

2. The apparatus of claim 1 wherein the diagnostic means comprises at least one chemical detector selected from the group consisting of a mass detector, an optical-based detector, a charged-mass detector, a thermal conductivity detector, an electron capture detector, and an immunoassay detector.

3. The apparatus of claim 2 wherein the mass detector is selected from a group consisting of a mass spectrometer, an acoustic wave detector or a quartz crystal microbalance.

4. The apparatus of claim 2 wherein the optical-based detector is selected from a group consisting of a infrared detector, an ultraviolet-visible detector, a refractive index detector, a fluorescence detector, a chemiluminescence detector, and a Raman detector.

5. The apparatus of claim 1 wherein the diagnostic means is selected from a group consisting of an ion-mobility spectrometer, a gas chromatograph, a high performance liquid chromatograph, a capillary electrophoresis chromatograph, a mass spectrometer, a Fourier-transform infrared spectrometer, a Raman spectrometer.

6. The apparatus of claim 1 wherein the inner probe additionally comprises a permeable screen that is placed over the adsorbent material.

7. The apparatus of claim 6 further comprising a means for pumping air from a region between the permeable screen and the adsorbent material to provide a pressure less than atmospheric air pressure.

8. The apparatus of claim 1 further comprising a means for introducing an aqueous solvent to a volume around the adsorbent material.

9. A method for detecting at least one semi-volatile explosive-indicating compound in subsurface soil, comprising, inserting an apparatus into subsurface soil, said apparatus comprising an inner probe having an adsorbent material contacting at least a portion of the surface of said inner probe, an outer sheath enclosing said inner probe, said outer sheath capable of being retracted to expose said inner probe and adsorbent material to subsurface soil when inserted under ground surface, means for desorbing in situ at least one semi-volatile, explosive-indicating compound attached to said inner probe, said means for desorbing in situ said at least one semi-volatile, explosive-indicating compound selected from a solvent, an inductive electrical circuit, a resistive electrical circuit, radiative energy, and a hot gas, and diagnostic means for detecting said at least one semi-volatile, explosive-indicating compound, said adsorbent material selected from the group consisting of polyethylene, polystyrene and polystyrene-divinylbenzene, said adsorbent material adsorbing at least one semi-volatile, explosive-indicating compound, said at least one explosive-indicating compound selected from the group consisting of octahydro-1,3,5,7-tetranitro-1,3,5,7-tetrazocine, hexahydro-1,3,5-trinitro-1,3,5-triazine, 1,3,5-trinitrobenzene, 1,3-dinitrobenzene, methyl-2,4,6-trinitrophenylnitramine, nitrobenzene, 2,4,6-trinitrotoluene, 2,4-dinitrotoluene, 2,6-dinitrotoluene, o-nitrotoluene, m-nitrotoluene, p-nitrotoluene, nitroglycerin, 4-amino-2,5-dinitrotoluene, 2-amino-4,6-dintrotoluene, and pentaerythritol tetranitrate;

desorbing in situ said at least one semi-volatile, explosive-indicating compound to produce a sample for analysis, analyzing said sample to detect the presence of said at least one semi-volatile, explosive-indicating compound.

10. The method of claim 9 further comprising the step of adding an aqueous solvent to the subsurface soil in contact with the adsorbent material.

11. The method of claim 9 wherein analyzing said sample to detect the presence of said at least one explosive-indicating compound is performed using a diagnostic means comprising at least one chemical detector selected from the group consisting of a mass detector, an optical-based detector, a charged-mass detector, a thermal conductivity detector, an electron capture detector, and an immunoassay detector.

12. The method of claim 10 wherein the aqueous solvent is added at a temperature above ambient temperature.

13. The method of claim 9 wherein analyzing said sample to detect the presence of said at least one explosive-indicating compound is performed using at least one diagnostic tool selected from the group consisting of an ion-mobility spectrometer, a gas chromatograph, a high performance liquid chromatograph, a capillary electrophoresis chromatograph, a mass spectrometer, a Fourier-transform infrared spectrometer, a Raman spectrometer.

* * * * *